United States Patent [19]

O'Neill

[11] 4,280,510
[45] Jul. 28, 1981

[54] SUTURELESS MYOCARDIAL LEAD INTRODUCER

[75] Inventor: Edward G. O'Neill, St. Paul, Minn.

[73] Assignee: Medtronic, Inc., Minneapolis, Minn.

[21] Appl. No.: 10,465

[22] Filed: Feb. 8, 1979

[51] Int. Cl.³ .............................................. A61N 1/04
[52] U.S. Cl. .................................. 128/784; 128/419 P
[58] Field of Search ............... 128/639, 642, 783, 784, 128/785, 790, 419 P

[56] References Cited

U.S. PATENT DOCUMENTS

| 3,827,428 | 8/1974 | Hon et al. | 128/642 |
| 3,875,947 | 4/1975 | Jula et al. | 128/785 |
| 3,910,271 | 10/1975 | Neward | 128/642 |
| 3,986,497 | 10/1976 | Dali | 128/642 |

FOREIGN PATENT DOCUMENTS 2732547 2/1979 Fed. Rep. of Germany ........... 128/785

*Primary Examiner*—William E. Kamm

*Attorney, Agent, or Firm*—R. Lewis Gable; John L. Rooney; Joseph F. Breimayer

[57] ABSTRACT

The sutureless myocardial lead introducer herein disclosed includes a handle having at the distal end thereof means for releasably holding a body tissue electrode for screwing into body tissue and is provided with a longitudinal slot extending toward the center of the handle and extending from adjacent the distal end thereof to the proximal end thereof to receive an insulated electric lead from the electrode. A hollow tube slides over the handle and holds the electric lead in place in the groove. A tunneling rod is slidably mounted within the handle and is provided with a fin which engages a locking slot at the proximal end of the handle. The fin may be disposed from a first position, wherein the fin is disposed in the locking slot, to a second position, wherein the tunneling rod engages the electrode to push the electrode clear of the handle, when the electrode has been screwed into the body tissue and when the tube has been removed from the handle releasing the electric lead from the slot in the handle.

7 Claims, 6 Drawing Figures

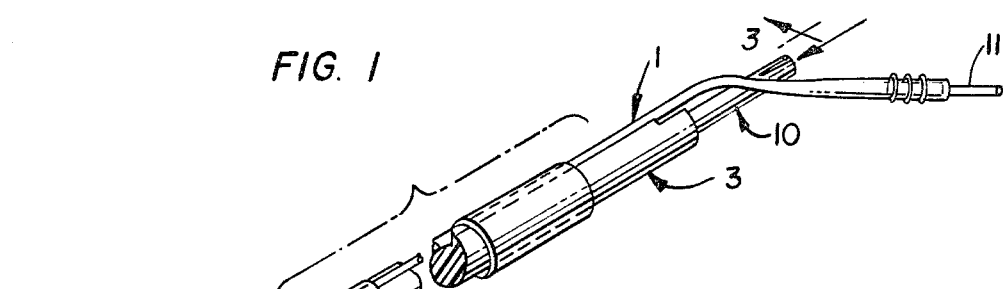
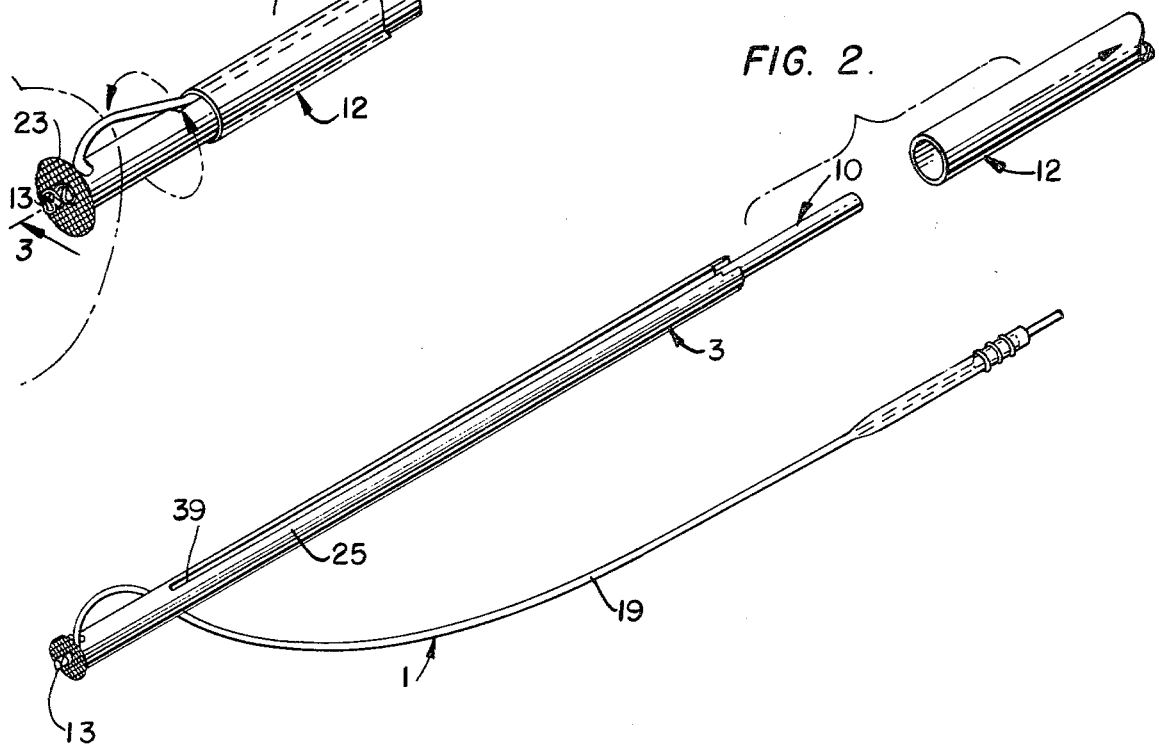
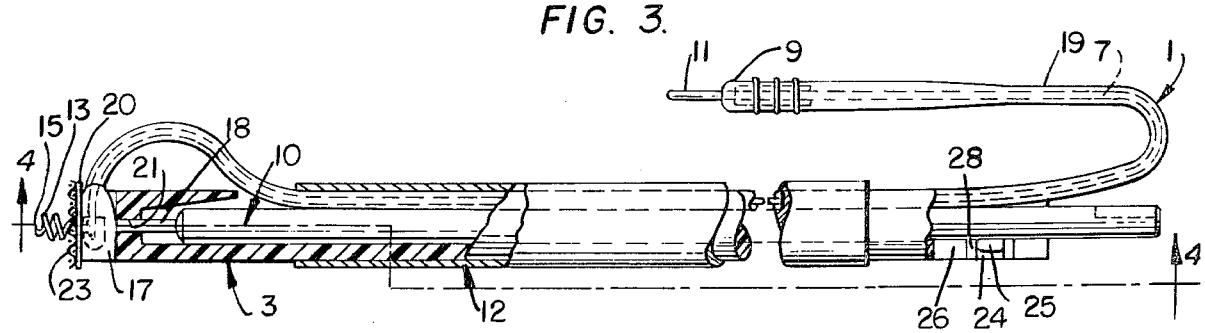
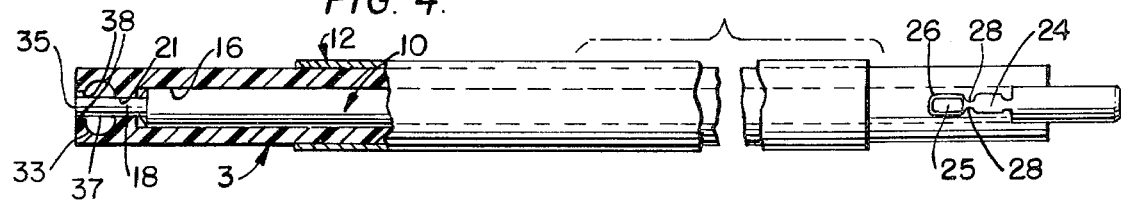

SUTURELESS MYOCARDIAL LEAD INTRODUCER

REFERENCE TO RELATED APPLICATION

U.S. Application Ser. No. 900,975, filed Apr. 28, 1978 by Edward G. O'Neill discloses a related device for screwing body tissue electrode into body tissue.

BACKGROUND OF THE INVENTION

1. Field of the Invention

This invention relates to the field of medical electronics and in particular to improved devices for handling electrical leads with a minimum of trauma to the body tissue in which the electrical leads are implanted.

2. State of the Prior Art

Electrical stimulation of body tissue and organs as a method of treating various pathological conditions is becoming quite commonplace. Such stimulation generally entails making some type of electrical contact with the body tissue or organ. In particular, with respect to the heart, electrical leads have been implanted by a thoracotomy in which an electrode formed on the end of the lead are physically implanted into the myocardial tissues.

Various electrode structures and various techniques for implanting those electrode structures into such body tissue as the heart or myocardium, have been developed. Typically, electrodes attached to the heart are stimulated by a cardiac pacemaker which may be implanted within the patient's body. Previously, a thoracotomy was commonly required to attach the cardiac pacemaker leads to the heart, and the electrical leads were sutured into electrical contact with the heart. This technique has numerous disadvantages. Firstly, a thoracotomy, which requires a large incision in the chest or thorax, is drastic surgery and has a relatively high mortality rate. Secondly, suturing the electrical leads into electrical contact with the heart causes severe trauma to the heart, which it is desired to minimize.

An intravenous connection has also been used to attach electrical leads of a cardiac pacemaker to the heart. In this technique, the electrical lead is passed through a vein into the heart where it is held by fibrilla located in close proximity to the heart valve through which the lead is passed. There are, however, many disadvantages to this technique also, including: the possibility of damage to the vein during insertion, such as vein perforation; the failure to attach securely the electrical lead to the heart; the possibility of perforating the heart wall with the electrical lead during insertion or after attachment has been completed; and the possibility of improper lead placement in the heart.

In U.S. Pat. No. 3,737,579, assigned to the assignee of this invention, there is disclosed a unipolar body tissue electrode comprising an uninsulated, conductive, rigid helix adapted for attachment to body tissue and a flexible insulated conductor having a proximal end adapted for connection to a pacemaker and a distal end for connection to the helical electrode. Further, the noted patent describes a device or auxiliary tool having an elongated, cylindrical configuration. At one end thereof there is provided a slot or cavity for receiving a raised portion or boot of the lead surrounding and housing a portion of the helical electrode, and further a groove aligned with the axis of the auxiliary tool for receiving in a tight, friction holding relationship at least a portion of the length of the lead's insulated conductor. The lead is mounted in the auxiliary device as indicated and the helical electrode is inserted by rotating the auxiliary tool. After the helical electrode has been inserted into the body tissue, the insulated conductor is stripped from the axially aligned groove and the boot is removed from the cavity.

In U.S. Pat. No. 3,875,947, assigned to the assignee of this invention, there is described an unipolar, tissue electrode similar to that described in U.S. Pat. No. 3,737,579, and further an improved auxiliary tool for facilitating the removal of the electrical lead from the primary tool after its helically shaped electrode has been inserted into body tissue, e.g., myocardium. In particular, the tool comprises a handle or primary tool of a substantially cylindrical configuration having a bore running along the axis thereof into which a secondary tool or tunneling rod is inserted, and a groove in communication with the bore extending also along the axis of the handle. The tunneling rod includes ridge or fin portions that are disposable in the groove and serve to remove the lead from the primary tool after electrode implantation. Further, the leading end of the tunneling rod is pointed to permit removal of the lead's boot that receives a portion of the helical electrode. In operation, the electrode is mounted as indicated above and the surgeon inserts the helical electrode by rotating the handle with the electrode mounted therein. After implantation, the surgeon inserts the tunneling rod into the bore directing the rod along the length of the handle whereby the fin is moved through the groove thus removing the lead's insulated conductor and upon full insertion, the leading end of the tunneling rod displaces the electrode's boot from the cavity.

As set out in an article entitled, "An Improved Introducer for the Sutureless Myocardial Pacemaker Lead", by Dr. Gerald M. Lawrie et al., appearing in *The Annals of Thoracic Surgery*, Volume 23, No. 5, May, 1977, a disadvantage of the inserting device of the U.S. Pat. No. 3,875,947 is that it requires a bimanual operation, i.e., the attending surgeon is required to grip the handle with one hand, while pushing forward the tunneling rod with his other hand to remove the insulated conductor. In addition, as the leading portion of the tunneling rod pushes the insulating boot of the electrode from the cavity, a rotating motion occurs, tending to displace the helical electrode within the myocardium, at right angles to the longitudinal axis of the handle. This unnecessary motion may cause myocardial trauma at the tip of the helical electrode, with subsequent fibrosis and threshold rise. To overcome these noted problems, this article suggests the adaptation of the inserting device of U.S. Pat. No. 3,875,947, by providing a series of fins in the tunneling rod and after insertion of the tunneling rod within the handling device, of placing the insulating conductor into the groove of the handle to form a plurality of loops. In addition, the leading end of the tunneling rod is shaped cylindrically whereby the attending surgeon may simply direct the tunneling rod forward with respect to the handle to remove the boot of the electrode lead, and to displace the insulated lead from the handle's slot with a single, unidirectional motion.

The present invention is an improvement over known lead introducers and has for its object to simplify the structure of such an introducer while providing for the easy removal of the lead from the handle by the simple movement of a sleeve off of the handle and at the same time providing for prevention of accidental dislodging of the electrode from the handle by accidental motion of a tunneling rod by providing locking for the tunneling rod in an inoperative position, while permitting an easy manual movement of the tunneling rod to a second operative position to engage and dislodge the electrode after it has been screwed into the body tissue. The introducer of the present invention is readily and easily introduced into the incision to the myocardium and after screwing the electrode into position in the myocardium, the actuation of the introducer to free the lead and to dislodge the electrode from the handle can, in most part, be performed manually by the thumb and forefingers of one hand without risk of dislodging the electrode from or imposing trauma upon the myocardium.

SUMMARY OF THE INVENTION

An insertion assembly for a sutureless myocardial lead introducer for attaching an electrode of a body implantable lead to body tissue has a flexible insulated electrical conductor extending from the electrode to a connector for a medical device and further has a hollow tubular rod means or handle with means at the distal end thereof for holding a portion of the lead adjacent the electrode in a position for attachment of the electrode to body tissue with a cylindrical tube defining a lumen for receiving the tubular rod means or handle during attachment of the electrode to body tissue and with further means for receiving an insulated portion of the insulator conductor for releasably holding the conductor along the length of the assembly during attachment of the electrode to body tissue and for releasing the conductor upon relative axial movement of the tubular means and the rod means. A tunneling rod is also utilized moving in the hollow handle for manually dislodging the electrode from the handle with locking means being provided in the handle for preventing accidental movement of the tunneling rod.

BRIEF DESCRIPTION OF THE DRAWINGS

In the accompanying drawings, in which like reference characters indicate like parts, a preferred embodiment of the present invention is shown and FIG. 1 is a view partially in section of an elevation of the assembly;

FIG. 2 is a view of the embodiment of FIG. 1 with the tube removed to show the handle and tunneling rod in operative position with the lead freed from the handle;

FIG. 3 is a side elevational view, partly in section, on the line 3—3 of FIG. 1;

FIG. 4 is a view from above, also partly in section, as seen on the line 4—4 of FIG. 3;

DESCRIPTION OF THE PREFERRED EMBODIMENT

Figure 5:
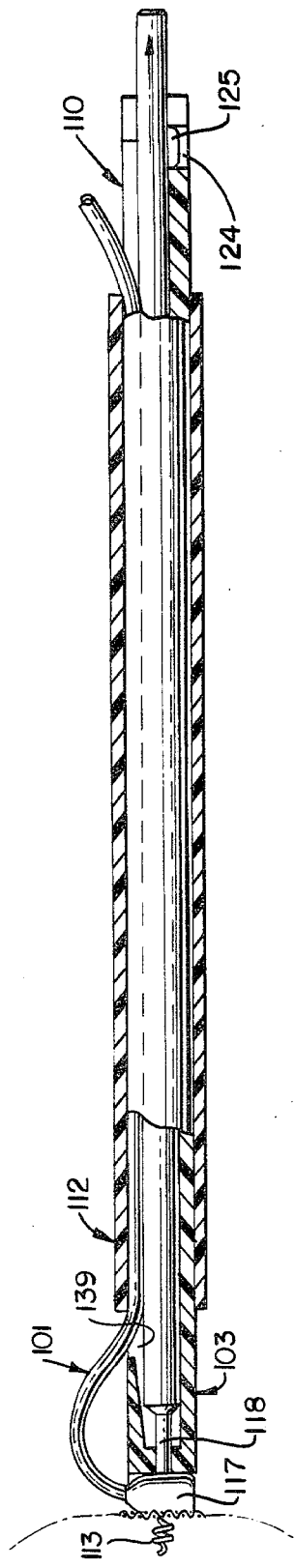
FIG. 5 is a side view, partly in section, of a further embodiment of this invention with the electrode screwed into place in the body tissue with its tube disposed about the handle and with the tunneling rod in position to displace the electrode from the handle.

As shown in FIG. 3, an implantable lead 1 is held by a handle 3. Lead 1, which is essentially the same as lead 10 depicted in FIG. 1 of U.S. Pat. No. 3,737,579, includes a flexible conductor 7 of wrapped platinum wire or other suitable conducting material adaptable to the internal environment of a human or animal body.

Affixed to the proximal end of conductor 7 is an electrical connector 9 having a tip or extension 11 which may be connected to a suitable implantable or external electrical medical device, e.g., a cardiac pacemaker. Affixed to and serving as the distal end portion of conductor 7 is an attachment means taking the illustrative form of a helical electrode 13 having several convolutions. Helical electrode 13 is a wire coil which may, for example, be made of platinum/iridium and terminates in a sharply pointed end 15 that is sufficiently rigid to be received into body tissue. Electrode 13 serves as the distal end portion of conductor 7 which may be screwed into body tissue as will be explained later. Electrode 13 and conductor 7 are electrically joined together by a conductive epoxy (not shown) substantially orthogonally with respect to one another and this electrical junction is contained in a rubber boot 17.

Conductor 7, connector 9 and boot 17 are covered with a relatively transparent, flexible, insulating covering being relatively inert with respect to the body, which, for example, may be a silicone rubber casing 19. The distal portion of casing 19 is terminated and shaped as a circular disc 20 through which helical electrode 13 projects. Helical electrode 13 projects through the disc 20 at substantially a right angle to conductor 7. Affixed to the under surface of the disc 20 is a circular sheet of netting 23, which may, for example, be made of Dacron ®, a trademark of E. I. DuPont DeNemours and Company for a type of polyester fiber. Netting 23 enhances fibrotic growth, further insuring a secure connection of the electrode to the tissue.

As shown in FIGS. 2, 3 and 4, the handle 3 is adapted to receive lead 1 at two places: the boot 17 and casing 19. Handle 3 comprises a substantially cylindrically-shaped body 25, made, for example, of a hard plastic material such a Delrin ®, a trademark of the E. I. DuPont DeNemours and Company for acetal resins. Preferably handle 3 should be made of an autoclavable material. Formed in a distal end of the handle 3 is a slot 33, which includes a frontal opening 35 leading to a cavity 37. The width of cavity 37 is greater than the width of its frontal opening 35. The widths of frontal opening 35 and cavity 37 are selected such that the boot 17 may be laterally compressed to a slight degree in order to pass through frontal opening 35. Once at least a portion of boot 17 is past a pair of shoulders 38, that portion resumes its original shape. To remove boot 17 from the cavity 37 requires recompressing such portion in order to gain withdrawal from the frontal opening 35. The shape of the cavity 37 and boot 17 is designed such that the force required to achieve the requisite compressive state is greater than the forces that might be encountered in the implantation procedure but insufficient to disturb the implanted electrode 13 as the boot 17 and handle 3 are being separated. A groove 39 is formed in the outer surface of the handle 3 and is disposed in a line substantially parallel to the axis of the handle 3 extending from its proximal end for substantially the entire length of the handle 3. Groove 39, which is aligned with the cavity 37 is adapted to loosely receive at least a portion of the length of casing 19, whereby the lead 1 is retained within the groove 39 by a tubularly shaped sleeve 12. The handle 3 includes a central bore that is disposed along the axis of the handle 3 extending from the proximal end of the handle 3 for substantially the entire length of the handle and is in communication via a centrally disposed passage 21 with the cavity 37.

A tubular or tunneling rod 10 is of an extended, cylindrical configuration and of appropriate diameter to be disposed within the central bore 16 of the handle 3. At the distal end of the tunneling rod 10, there is a portion 18 of reduced diameter as shown in FIGS. 3 and 4, adapted to pass through the passageway 21 and into the cavity 37. As shown in FIG. 3, the portion 18 is adapted to extend into the cavity 37 to make contact with the boot 17 of the lead 1, whereby as will be explained in detail later, the boot 17 may be ejected from the handle 3. At its proximal end, the tunneling rod includes a fin 25, which is spaced an appropriate distance from the proximal end of the tunneling rod 10, as shown in FIGS. 3 and 4. The handle 3 has a plurality of aligned, contiguous slots 24 and 26 for receiving the fin 25. The slots 24 and 26 are aligned with the axis of the handle 3 and are disposed on the opposite side of the handle 3 with respect to its slot 39. A pair of notches 28 separate the slots 24 and 26 and serve to retain the fin 25 within the first notch 24. Upon depressing the proximal end of the tunneling rod 10, the fin 25 with increased pressure upon the tunneling rod 10, is disposed from the first slot 24 to the second slot 26 past the pair of notches 28. As shown in FIG. 3, the tunneling rod 10 is disposed in a first position, wherein its fin 25 is disposed in the first slot 24. In the first position, the tunneling rod 10 is disposed within the handle 3 so that its end portion 18 abuts but does not extend into the cavity 37. Thus, as shown in FIG. 3, in the first position, the boot 17 of the lead 1 is retained within the cavity 37.

In order to prepare the lead introducer of the present invention, the boot 17 of the lead 1 is first inserted into the proximal end of the handle 3 and in particular into its cavity 37. At this stage of preparation, the lead assembly is essentially as shown in FIG. 2. Next, the casing 19 as it extends from the distal end of the handle 3, is disposed within the slot 11, wherein it is loosely received. Next, the tube 12 is inserted about the handle 3, thus forming the lead introducer assembly as shown in FIG. 1, with the tube 12 holding the lead 1 within the groove 39 of the handle 3.

In the course of the surgical procedure for implanting the medical device and in particular a heart pacer, an incision is first made into the chest or abdominal cavity of the patient. Thereafter, with the body tissue and in particular the heart tissue exposed, the lead introducer is disposed through the incision to bring the electrode 13 into position adjacent the body tissue or myocardium. Then the lead introducer is rotated three or four turns to engage and to insert the electrode 13 into the body tissue to secure the electrode in place. Next, with the tube 12 still in place about the handle 3, as shown in FIG. 1, the attending physician with but a single hand, grips the sides of the handle 3 between two forefingers and with his thumb presses the tunneling rod 10 in a direction in accordance with the arrow of FIG. 1, moving the tunneling rod 10 from its first position as shown in FIG. 3 to its second position, as shown in FIG. 4. As indicated in FIG. 4, in its second position, the fin 25 is moved from the first slot 24 to the second slot 26, and the portion 18 of the tunneling rod 10 is fully inserted into the cavity 37, thereby ejecting the boot 17 from the handle 3. It is noted that when the fin 25 is disposed in either of the slots 24 or 26, that it is held within the slot or notch, thereby retaining the tunneling rod 10 within the handle 3 so that it does not accidentally fall out of the handle 3. Thereafter, the tube 12 is removed as by sliding rearwardly of the handle 3. Since the casing 19 of the lead 1 is only loosely held within the groove 39, it is freely removed therefrom without imposing any resultant strain or trauma upon the electrode 13 or the patient's tissue.

Figure 6:
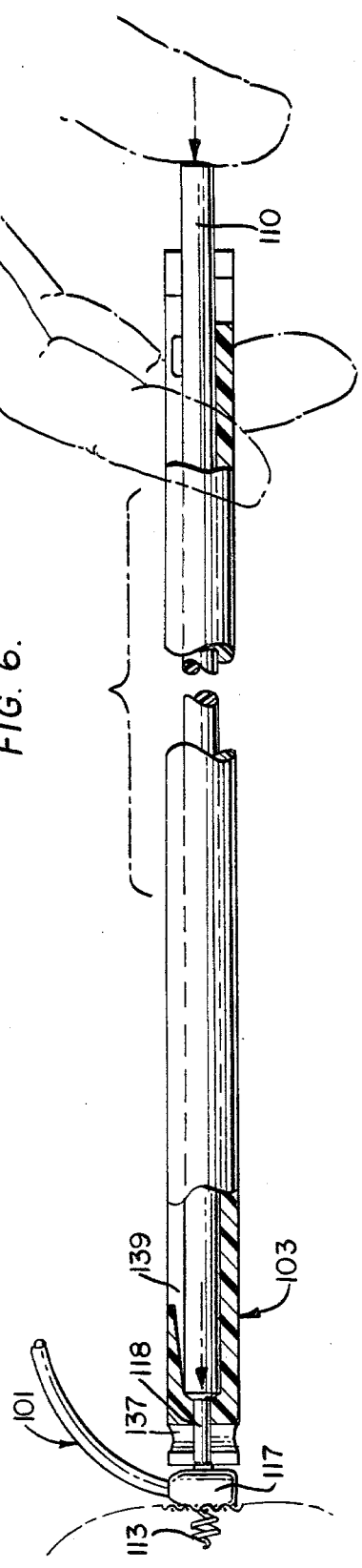
FIG. 6 is a view similar to that of FIG. 5 showing the manual operation of the tunneling rod to remove the electrode from the handle.

In a further embodiment of this invention, as shown in FIGS. 5 and 6, where like elements have similar numbers but numbered in a 100 series, there is shown an alternative embodiment of this invention, where there is included but a single slot 124 for receiving and holding the fin 125 in the first position. Initially as shown in FIG. 5, the lead introducer of the alternative embodiment is inserted within the incision with the tube 112 holding the lead 101 in slot 139 and the boot 117 disposed within the cavity 137 of the handle 103 and the tunneling rod 110 locked in a fixed relationship with the handle 103 with its fin 125 in the slot 124. This lead introducer is inserted through the incision to bring the electrode 113 into position adjacent the body tissue or myocardium, and the introducer is rotated manually to engage the electrode 13 into the body tissue thus securing the electrode 113 in place. Next, the tube 112 is manually removed from the handle 103 by a sliding movement in the direction of the arrow as seen in FIG. 5, thus freeing the lead 101 from the slot 139. Next, the physician grasps the proximal end of the tunneling rod 110 withdrawing it to the right as seen in FIG. 6 thereby disengaging the fin 125 from the slot 124 and thereafter, rotating the tunneling rod 110 180° until the fin 125 is aligned with the slot 139. Thereafter, the physician grasps the handle 103 as shown in FIG. 6 with his fingers, placing his thumb against the proximal end of the tunneling rod 110, and pressing it to the left in the direction of the arrow, whereby the portion 118 is inserted within the cavity 137 to eject the boot 117 of the lead 101. Thereafter, the handle 103 and the tunneling rod 110 may be withdrawn from the incision, and the lead 101 connected to any suitable medical device.

The manual operation required to activate the lead introducer of this invention and in particular its tunneling rod for movement of its fin from its slot or slots and for disengagement of electrode from the handle, is conveniently and easily done manually by one hand utilizing the forefingers and thumb this preventing any accidental withdrawal of electrode from the body tissue. It should further be noted that the lead is easily freed from the slot in the handle by the removal of sleeve again preventing any accidental dislodgment of electrode from the body tissue, hence no force is imposed on the body tissue for this purpose and the tunneling rod acts only to free the electrode from the handle and performs no function in removal of the lead from the slot in the handle.

Changes may now be suggested to those skilled in the art in the improved insertion assembly of the present invention for attaching an electrode to a body tissue without departing from the inventive concept and reference should therefore be had to the appended claims to determine the scope of this invention.

What is claimed is:

1. A body implantable lead and lead insertion assembly for use in attaching an electrode of said body implantable lead to body tissue, said lead including a flexible insulated electrical conductor extending between said electrode and a connector adapted to be connected to a medical device, said insertion assembly comprising:

(a) tubular rod means having first means at the distal end thereof for holding a portion of said lead adjacent said electrode in a position for attachment of said electrode to body tissue;

(b) cylindrical tube means defining a lumen; and (c) slot means configured for loosely receiving an insulated portion of said insulated conductor for releasably containing said conductor along the length of said assembly during attachment of said electrode to body tissue and for releasing said conductor upon relative axial movement of said tubular means and said rod means, said lumen being configured for loosely receiving said tubular rod means and retaining said insulated portion within slot means during attachment of said electrode to body tissue and thereafter for permitting the ready withdrawal of said tubular rod means from said lumen whereby said insulated portion may be readily withdrawn from said slot means.

2. An assembly as described in claim 1, further including a tunneling rod mounted for manually actuated sliding movement in said tubular rod means for forcing said electrode from said holding means.

3. An assembly as described in claim 2, further including a fin on said tunneling rod, and a first slot in said rod means removably holding said fin and said tunneling rod in a first, relative position to each other.

4. An assembly as described in claim 3, wherein said slot means comprises a longitudinal slot in said rod means diametrically opposite said first slot for receiving said fin during manual actuation of said tunneling rod and for receiving said insulated conductor during attachment.

5. An assembly as described in claim 1, wherein said slot means comprises a slot disposed along the axis of said tubular rod means for receiving and holding said insulated portion of said insulated conductor in a substantially friction-free relationship.

6. An assembly as claimed in claim 1, wherein said slot means comprises an elongated slot disposed in said tubular rod means for releasably receiving said insulated portion of said insulated conductor in a substantially friction-free relationship, said cylindrical tube means being configured to be disposed about said tubular rod means retaining said insulated portion of said insulated conductor within said groove during attachment of said electrode to body tissue and for being removed from said tubular rod means to permit the release of said insulated conductor from said groove with minimum affect upon said electrode.

7. An assembly as claimed in claim 6, wherein said electrode is of a spiral configuration.

* * * * *